(12) United States Patent
Hara et al.

(10) Patent No.: US 7,695,141 B2
(45) Date of Patent: Apr. 13, 2010

(54) OCULAR LIGHT STIMULUS APPARATUS (75) Inventors: Takuya Hara, Hamamatsu (JP);
Kazunori Matsumura, Hamamatsu (JP); Tatsuya Fujii, Hamamatsu (JP);
Masaharu Mizuochi, Hamamatsu (JP)

(73) Assignee: Kowa Company Ltd. (JP)

( * ) Notice: Subject to any disclaimer, the term of this patent is extended or adjusted under 35 U.S.C. 154(b) by 0 days.

(21) Appl. No.: 12/283,637

(22) Filed: Sep. 12, 2008

(65) Prior Publication Data
US 2009/0231543 A1 Sep. 17, 2009

(30) Foreign Application Priority Data
Mar. 13, 2008 (JP) ............................. 2008-063874
Apr. 10, 2008 (JP) ............................. 2008-102431

(51) Int. Cl.
*A61B 3/10* (2006.01)
(52) U.S. Cl. ........................................ 351/221; 351/213
(58) Field of Classification Search ................. 361/200, 361/205, 206, 213, 214, 221, 245
See application file for complete search history.

(56) References Cited
FOREIGN PATENT DOCUMENTS
JP 2005-323815 * 11/2005

* cited by examiner

*Primary Examiner*—Jack Dinh
(74) *Attorney, Agent, or Firm*—Adams & Wilks (57) ABSTRACT

A stimulus light from a stimulus light source is projected to the retina of an ocular fundus under examination to stimulate the retina in localized fashion to generate a bioelectric signal from the retina. The stimulus light source is mounted on a movable block, and an operating lever is used to move the stimulus light source to change the stimulus light on the retina. The size of the stimulus light can also be varied using a panel having a plurality of openings with different diameters for allowing the stimulus light to pass through. This assures a reliable local ERG examination because the bioelectrical signal can be produced in a wider area of the retina. The operating lever is further fixed by inserting a cap to keep the projected stimulus light unchanged. This allows the burden on the examiner to be reduced remarkably, assuring a reliable local ERG examination.

11 Claims, 7 Drawing Sheets

OCULAR LIGHT STIMULUS APPARATUS

BACKGROUND OF THE INVENTION

1. Field of the Invention

The present invention relates to an ocular light stimulus apparatus, and more particularly relates to an ocular light stimulus apparatus for providing localized light stimulus to a retina of an ocular fundus under examination by stimulus light from a stimulus light source to perform biological examination through use of a bioelectrical signal from the retina.

2. Description of the Prior Art

Conventional known methods used primarily for ophthalmic examination include not only capturing a fundus image and performing fundus examination, but also electroretinogram (ERG) examination in which stimulus light is radiated to a retina, an action potential generated in the retina is measured, and an electroretinogram is created to perform an ophthalmic biological examination.

In an ERG examination, a background light is needed for illuminating the background onto which the stimulus light is radiated, and the quality of the ERG examination is determined by the proper combination of background light intensity and stimulus light intensity. Japanese Journal of Ophthalmology, Vol. 92, No. 9 (Sep. 10, 1988, 5-(1423) to 11-(1429)) describes the effects obtained from an ERG examination (local ERG) when stimulus light is radiated in localized fashion to a point on the macula of the fundus using visible background light.

Japanese Examined Patent Application Publication No. 1987-16090 discloses a light stimulus apparatus in which stimulus light is radiated to an ocular fundus under examination using a fundus camera, and electrical information obtained through the light stimulus is displayed as an electroretinogram. Japanese Examined Patent Application Publication No. 1987-20809 proposes a technique for observing which portions are stimulated in what manner by local ERG stimulus light while observing a wide range of the fundus by infrared light.

Furthermore, Japanese Examined Patent Application Publication No. 1992-19852 discloses that an ocular fundus under examination is observed without dilation, and a beam of light for observing and imaging the eye under examination is used as stimulus light. Japanese Laid-open Patent Application No. 2005-323815 discloses that a light stimulus apparatus for radiating stimulus light to a fundus is attached as a unit to a fundus camera to perform ERG examination. Japanese Laid-open Patent Application No. 2006-42952 discloses that, to perform local ERG examination, the entire retinal area is irradiated by white light using a white-light-emitting diode with this illumination used as a background, and a stimulus light spot is radiated from a high-luminance light-emitting diode while observing the fundus by infrared light.

In an ophthalmic examination apparatus, a light source (fixation lamp) used for ophthalmic examination is moved on a plane perpendicular to the optical axis (Japanese Laid-open Patent Application No. 1987-144635 and Japanese Patent No. 2736780).

In the conventional techniques, the position of the stimulus light source or the size of the stimulus light is not varied when the local ERG examination is performed, and as a result, drawbacks occur in that a bioelectric signal is not obtained from an arbitrary position of the retina, and a reliable local ERG examination is difficult to perform.

When the stimulus light projection position is varied in the local ERG examination, drawbacks also occur in that the projection position is not easily maintained at a prescribed position, and a reliable bioelectric signal is difficult to obtain from the retina.

It is therefore an object of the invention is to provide an ocular light stimulus apparatus capable of performing a reliable local ERG examination with a simple structure.

SUMMARY OF THE INVENTION

An ocular light stimulus apparatus according to the invention is adapted for use in providing localized light stimulus to a retina of an ocular fundus under examination to perform biological examination through use of a bioelectrical signal from the retina. The ocular light stimulus apparatus comprises a stimulus light source for emitting stimulus light to provide the localized light stimulus to the fundus under examination; a movement mechanism for moving the stimulus light source to change a projection position of the stimulus light on the fundus; and a stimulus light size changing mechanism for changing a size of the stimulus light from the stimulus light source.

In the invention, the position of the stimulus light source and the size of the stimulus light can be varied, so that a bioelectrical signal can be obtained from the various areas of the retina of the eye under examination, thus assuring a reliable local biological examination.

Furthermore, the ocular light stimulus apparatus comprises a stimulus light source for emitting stimulus light to provide the localized light stimulus to the fundus under examination; a movement mechanism for moving the stimulus light source to change a projection position of the stimulus light on the fundus; an operating member operated to act on the movement mechanism to change the projection position of the stimulus light; and a fixing member for fixing the operating member.

In the invention, it is possible to fix the operating member that is operated so as to move the stimulus light source, so that the movement of the projected stimulus light can be locked. This allows the burden on the examiner to be alleviated and a reliable local ERG examination to be performed.

Further features of the invention, its nature and various advantages will be more apparent from the accompanying drawings and following detailed description of the invention.

BRIEF DESCRIPTION OF THE DRAWINGS

FIG. 5 is a sectional view along line A-A' in FIG. 4a;

DESCRIPTION OF THE PREFERRED EMBODIMENTS

The present invention will now be described in detail with reference to the embodiments shown in the attached drawings.

Figure 1:
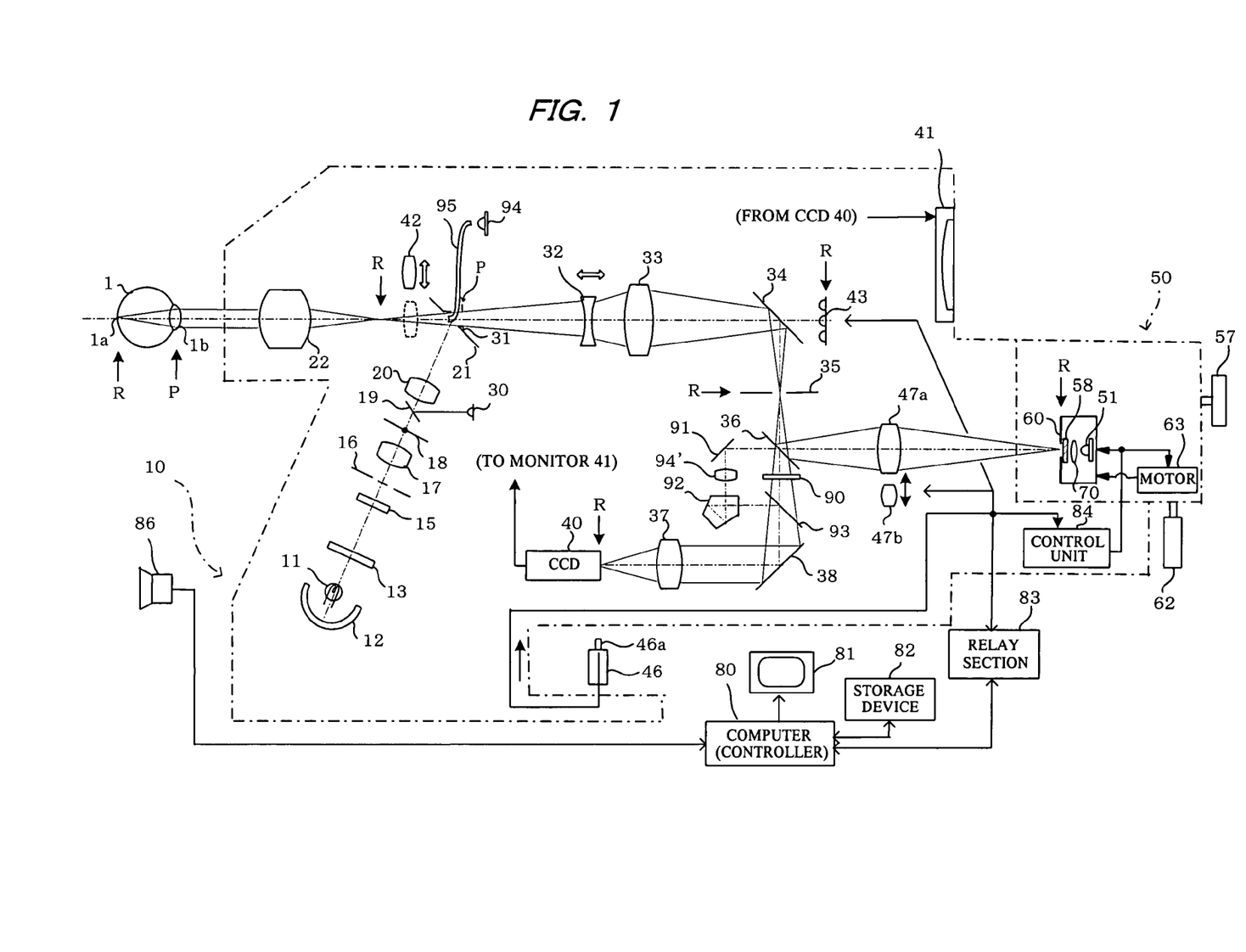
FIG. 1 is a schematic structural view showing the overall structure of an ophthalmic light stimulus apparatus of the present invention.

FIG. 1 shows an ocular light stimulus apparatus that comprises a light stimulus unit 10 and a stimulus light source unit 50. In FIG. 1, the reference symbol R indicates the position conjugate with a fundus 1a of an eye 1 under examination, and the reference symbol P indicates the position conjugate with the anterior ocular segment 1b (particularly the pupil) thereof.

The light stimulus unit 10 is provided with an illumination optical system for illuminating the fundus of the eye under examination, and an imaging optical system for imaging the illuminated fundus. In the illumination optical system, light emitted from a halogen lamp or other illumination light source 11, and light reflected by a concave mirror 12 are converted to infrared light via a visible-cutting infrared-transmitting filter 13 and directed into a diffusing plate 15 that diffuses the transmitted infrared light. A ring slit 16 is disposed in the conjugate position P with the anterior ocular segment (pupil) 1b of the eye 1 under examination. The illumination light from the ring slit 16 passes through a lens 17 and a black spot plate 18 for removing reflection of an objective lens 22, as well as through a half mirror 19 and a relay lens 20. After the illumination light is reflected by a total reflection mirror 21 having an aperture in the center thereof, the light is directed through the objective lens 22 into the fundus 1a from the anterior ocular segment 1b of the eye 1 to illuminate the fundus 1a thereof by infrared light.

The reflected light from the fundus 1a is received via the objective lens 22, and passes through the aperture in the total reflection mirror 21, a photographic stop 31 disposed in the position P conjugate with the anterior ocular segment, a focus lens 32, and an imaging lens 33. The light is then reflected by a half mirror 34 and directed into a half mirror 36 via a field stop 35 disposed in the position R conjugate with the fundus 1a. The infrared light that has passed through the half mirror 36 is reflected by a mirror 38, passes through an imaging lens 37, and impinges on an imaging device 40 disposed in the fundus conjugate position R. The imaging device 40 is composed of an infrared CCD or the like sensitive in the infrared and visible light regions, and produces a signal that is inputted to a monitor 41.

A stimulus light source unit 50 is attached to the light stimulus unit 10. The unit 50 includes a stimulus light source 51 composed of a light-emitting diode or the like for emitting visible light. The stimulus light source 51 is fixed inside a cavity 52a formed in a movable block 52, as shown in detail in FIG. 2. Protrusions 52b, 52c are formed on the movable block 52, and the protrusions 52b, 52c are fitted into a circumferential groove 53a formed in a housing 53 of the light source unit 50. The movable block 52 is supported by a spherical body 54 that is attached to one end of an operating lever 57. The lever 57 is provided with a spherical body 55 that is supported by a bearing 56 fixed to the housing 53. The lever 57 can be operated to move the movable block 52 in a plane x-y perpendicular to the optical axis via the spherical bodies 54 and 55.

Figure 2:
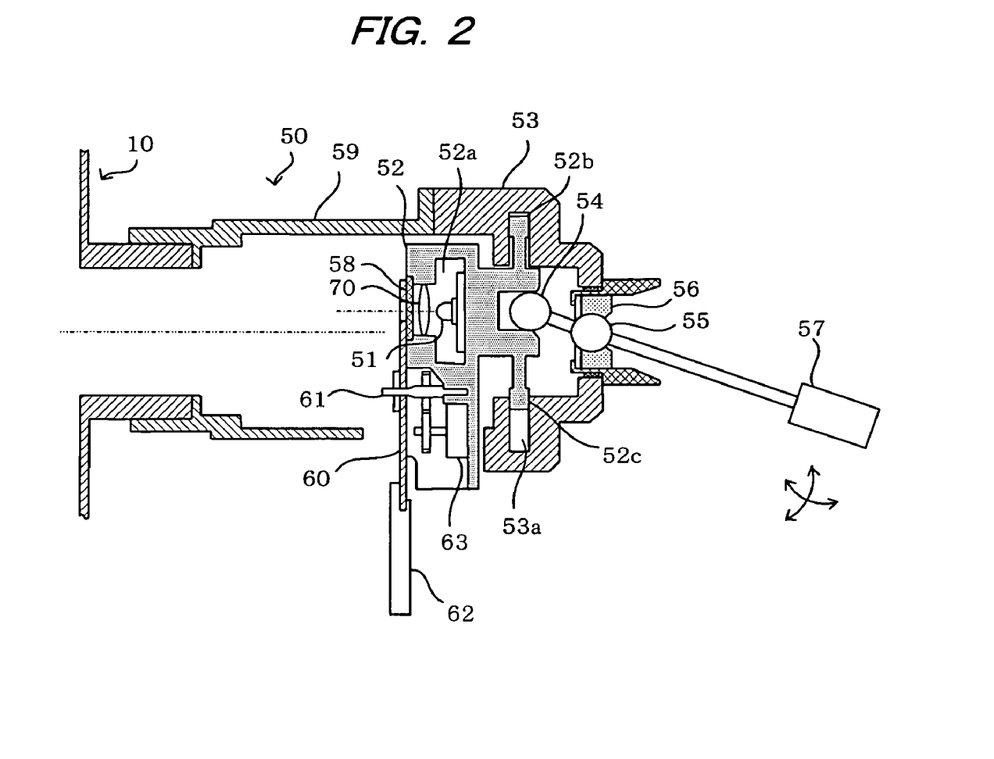
FIG. 2 is a sectional view showing the detailed structure of a stimulus light source unit.
Figure 3:
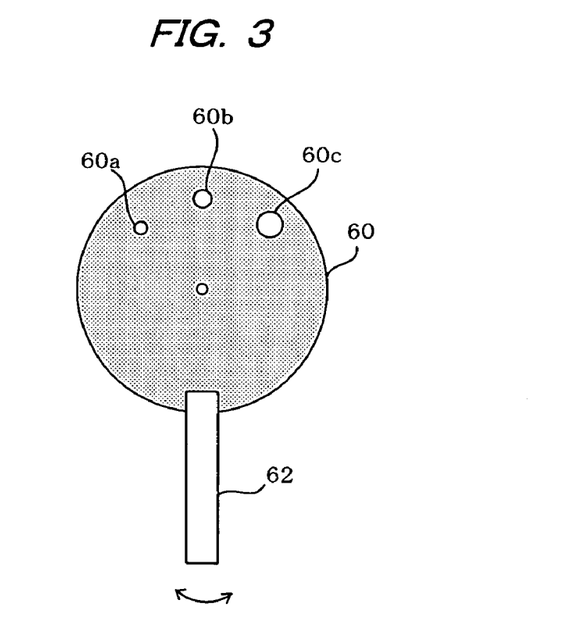
FIG. 3 is a front view showing an indicator disk shown in FIG. 2.

An indicator disk 60 is attached to the movable block 52 via a shaft 61 mounted on the movable block 52. A plurality of openings 60a, 60b, 60c having different diameters is formed in the indicator disk 60 as shown in FIG. 3. The indicator disk 60 can be rotated about the shaft 61 manually through the use of a lever 62 fixed to the indicator disk 60, or through the use of a motor 63 fixed to the movable block 52 to bring any of the openings into a position in which it faces the stimulus light source 51 and a diffusing plate 58. The operation of the lever 62 allows the spot diameter of the stimulus light to be varied and the operation of the lever 57 allows the stimulus light to be positioned in the x-y plane.

The stimulus light source unit 50 is attached to the light stimulus unit 10 via a cylindrical housing 59 fixed to the housing 53 so that the indicator disk 60 is disposed in the position R conjugate with the fundus, as shown in FIG. 1.

Operating a switch 46a provided to a joystick 46 causes the stimulus light source 51 to be turned on by a control unit 84 to emit stimulus light, which impinges on the diffusing plate 58 via a lens 70. The stimulus light diffused by the diffusing plate 58 is set to a prescribed spot size by the openings 60a through 60c of the indicator disk 60. The stimulus light then passes through a variable-power lens 47a (47b) and impinges on the half mirror 36. The visible-light reflected by the half mirror 36 is projected as stimulus light to the fundus 1a from the pupil 1b of the eye under examination via the half mirror 34, the lenses 33, 32, the aperture of total reflection mirror 21, and the objective lens 22.

An ERG electrode 86 is attached to the eye 1 under examination. A signal from the electrode 86 is inputted to a control computer (personal computer) 80 provided with a display device 81 and a storage device 82. The electroretinogram created in the computer 80 is displayed by the display device 81 or stored by the storage device 82.

In order for a projection index (stimulus light) from the stimulus light source 51 to be observed and displayed on the monitor 41, the visible light from the stimulus light transmitted by the half mirror 36 is reflected by the mirror 38 via a mirror 91, a lens 94', a prism 92, and an infrared-transmitting visible-reflecting mirror 93, and directed into the imaging device 40.

To prevent the visible light from the stimulus light source 51 that is divided and reflected by the half mirror 36 from being reflected by the surface of the imaging lens 33 and returned as reflected light into the imaging device 40, a filter 90 for reflecting visible light and transmitting infrared light is inserted between the half mirror 36 and the infrared-transmitting visible-reflecting mirror 93. Since the filter 90 has infrared-transmitting characteristics, the observation light is directed into the imaging device 40 without being cut by the filter 90.

A light source 94 for working distance (hereinafter referred to as the WD light source) is provided for alignment. The WD light source 94 is composed of a light-emitting diode for emitting both visible light (white light) and infrared light, for example. The beam of light from the WD light source 94 is directed via an optical fiber 95 to the vicinity of the center of the aperture of the total reflection mirror 21 to form a working distance indicator. The working distance indicator is projected by the objective lens 22 to the cornea of the eye 1 under examination. When the working distance is correct, the beam of light frontally reflected by the cornea of the eye 1 is substantially afocal.

The WD light source 94 is also used as a light source for the background light used for the local ERG examination. The light beam from the WD light source 94 is projected as background light to the fundus 1a via the anterior ocular segment 1b to illuminate the fundus 1a by visible light. The light intensity of the WD light source 94 at this time is set to a different intensity than the alignment light intensity for adjusting the working distance.

The illumination optical system is provided with a focusing light source 30 composed of an infrared LED for producing a focusing beam. The infrared light from the light source 30 is incident on the fundus 1a as a focus dot via the half mirror 19. The position of the focus dot on the fundus is changed according to the movement of the focus lens 32, and the examiner can bring the fundus into focus by observing the focus dot. In the initial stage of alignment, an anterior ocular segment lens 42 is inserted, and the examiner can therefore confirm image of the anterior ocular segment 1b of the eye 1 under examination on the monitor 41. During the alignment or focusing operation, an internal fixation lamp 43 is turned on, and the examiner can make certain of the alignment or focusing operation by calling the attention of the examinee to the fixation lamp.

The computer (control unit) 80 can set various measurement conditions in order to perform the local ERG examination. The measurement conditions include the intensity (amount of light) of the background light from the WD light source 94, the intensity (amount of light) of the stimulus light from the stimulus light source 51, the wavelength components of the background light and the stimulus light, the spot diameter (positions of the openings 60a through 60c of the indicator disk 60) of the stimulus light, the radiation time (lamp-on time) of the stimulus light, the number of radiations of the stimulus light, the blink period (when blinking is performed even in the alignment state) of the stimulus light, the position of the fixation lamp 43, and so on.

A relay section 83 is provided between the light stimulus apparatus and the computer 80 in order to synchronize retinal stimulus with the measurement condition set by the computer 80. The relay section 83 may be provided within the light stimulus apparatus.

The procedure by which the local ERG examination is performed in such a configuration will be described hereinafter.

A measurement condition such as described above is set prior to the examination. When the illumination light source 11 is turned on, the fundus 1a is illuminated by infrared light. The anterior ocular segment lens 42 is inserted, and an image of the anterior ocular segment is observed to perform alignment by the anterior ocular segment as needed. The anterior ocular segment lens 42 is then retracted from the optical path, and the WD light source 94 is turned on to perform alignment for adjustment of the relative position between the eye under examination and the light stimulus apparatus.

The light from the WD light source 94 is radiated via the optical fiber 95 to the cornea of the eye 1 as alignment light for adjusting the working distance. Radiation of visible light of white light components is basically unnecessary during alignment, but when visible background light is suddenly radiated at the start of measurement, a stimulus that can be considered strong is imparted to the examinee. This may cause the initial data to be unstable. For this reason, visible light is preferably radiated prior to measurement at an intensity that is equivalent to that at the time of measurement, or visible light of the weakest intensity is radiated that is necessary for the stable initial data to be obtained at the time of measurement. Since the WD light source 94 thus radiates visible light and infrared light even during alignment, the infrared light component of the reflected light from the cornea passes through the half mirror 36, and is received by the imaging device 40. This allows the examiner to observe the corneal reflected light through the use of the monitor 41. When the working distance is correct, the beam of light frontally reflected by the cornea is substantially afocal. Therefore, alignment (adjustment of the working distance) of the optical axis direction (Z direction) is performed so that the corneal reflection image can be observed as a spot. On the other hand, alignment of the directions (X, Y directions) perpendicular to the optical axis is performed using the joystick 46 so that the corneal reflection image is substantially at the center of the fundus image.

The infrared focus dot from the focusing light source 30 enters the fundus 1a via the half mirror 19, and the focus dot position changes according to the movement of the focus lens 32. Therefore, the examiner can bring the eye under examination into focus by observing the focus dot on the monitor 41. During the alignment or focusing operation, the internal fixation lamp 43 is turned on, and the examiner can make certain of the alignment or focusing operation by calling the attention of the examinee to the fixation lamp.

When the alignment and focusing operations are completed, the switch 46a is operated, and the local ERG examination is initiated. At this time, the background light and stimulus light from the WD light source 94 and the stimulus light source 51 are set to the desired brightness and/or wavelength component in accordance with the measurement conditions transmitted via the relay section 83. The set measurement conditions and the like are displayed by the display device 81, but cannot be displayed by pressing a specific button, if the displaying may disturb the alignment.

At the time of the local ERG examination, infrared light is unnecessary, but it is possible for misalignment to occur due to poor fixation of the eye under examination during examination, and infrared light is therefore radiated during examination as well so that the working distance can be confirmed.

The stimulus light obtained from the stimulus light source 51 is turned on for a prescribed time set as a measurement condition. The stimulus light is thus radiated as visible light via the half mirror 36 to the fundus 1a that is irradiated with background light. The radiation position of the stimulus light can be changed by operating the lever 57, and the spot size of the stimulus light can be changed by selecting any of the openings 60a through 60c by rotating the indicator disk 60 through the use of the motor 63 or by operating the lever 62. In addition, the variation range can be widened, and the balance between the spot size and the intensity (amount of light) of the stimulus light can be varied through joint use of variable-power lenses 47a, 47b.

When the stimulus light is radiated to the fundus, an action potential is generated in the retina. The ERG electrode 86 detects the potential generated, which is inputted to the computer 80 to create an electroretinogram.

The stimulus light is also radiated in advance at the time of alignment so that the examiner can distinguish the location being stimulated when alignment is completed. At this time, the stimulus light is blinked at a prescribed blinking period that is set as a measurement condition, so as not to be mistaken for the focus dot, the working dot, or the like. When the stimulus light is difficult to recognize at the prescribed blinking period set as the measurement condition, a blinking period for alignment is set that is easier to recognize. The beam of the stimulus light transmitted by the half mirror 36 is reflected by the mirror 38 via the mirror 91, the prism 92, the lens 94', and the infrared-transmitting visible-reflecting mirror 93, and directed into the imaging device 40. The examiner can therefore recognize the portion of the eye under examination to which the stimulus light is being radiated.

The intensity (brightness) of the stimulus light also depends on the intensity of the background light, so that the intensity of the stimulus light is set to an intensity whereby an action potential is generated in the retina. The stimulus light is radiated during alignment as well. Since the stimulus light is used at the time of alignment merely to determine the position to which the stimulus light is being radiated, the stimulus light is set to an intensity weaker than the intensity thereof during the local ERG examination.

When the stimulus light is radiated the number of times set as the measurement conditions, the local ERG examination is completed. The electroretinogram created by the computer 80 is displayed by the display device 81 and stored by the storage device 82.

In the alignment state during the local ERG examination, the stimulus light is blinked at the prescribed blinking period as described above, and the position of the stimulus light during measurement can be confirmed in advance without mistaking the stimulus light for the working dot or the like. The examiner can therefore modify the appropriate alignment while observing the fundus of the examinee. When the examinee is significantly misaligned, the local ERG examination can be stopped by pressing and holding the switch 46a once more.

The stimulus light source 51 is used to generate the stimulus light in the embodiment described above, but a liquid crystal display device (LCD) may also be disposed in the fundus conjugate position R instead of the stimulus light source 51 to perform the local ERG examination. Since the liquid crystal display device is connected to the computer 80 via the control unit 84 and the relay section 83, an indicator can be displayed by a display device (not shown). The displayed indicator is projected as stimulus light to the fundus of the eye under examination.

Figure 4A:
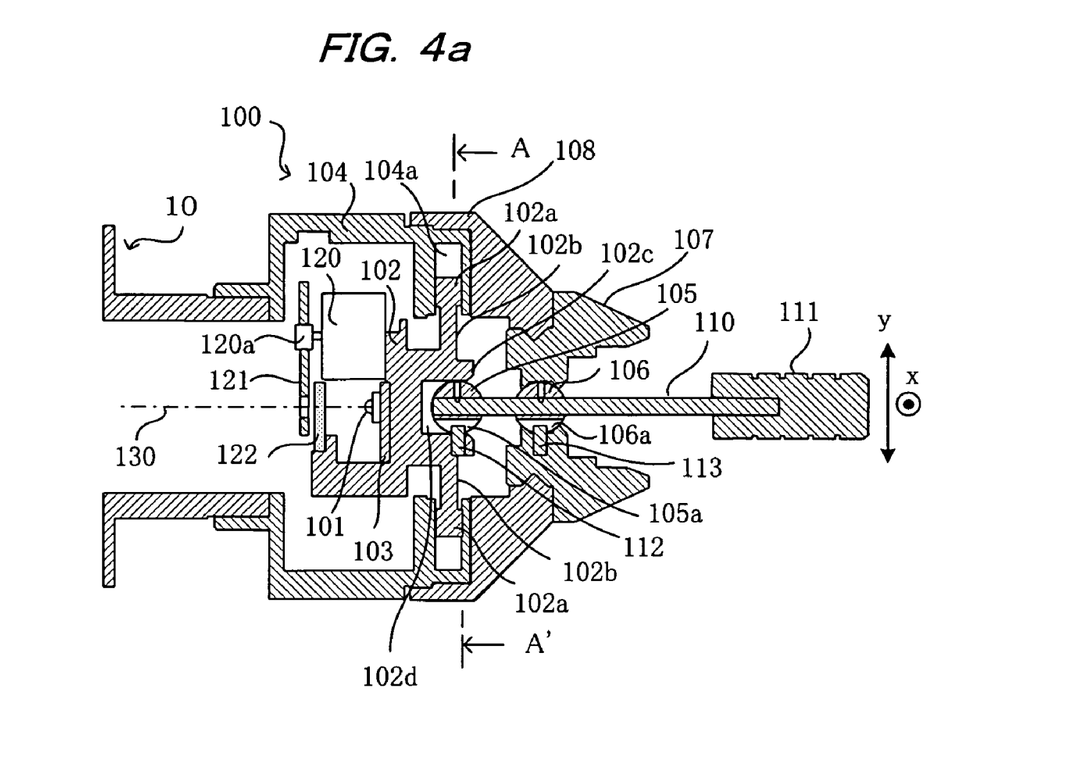
FIG. 4a is a longitudinal sectional view showing the stimulus light source unit when an operating lever is in the center position.
Figure 4B:
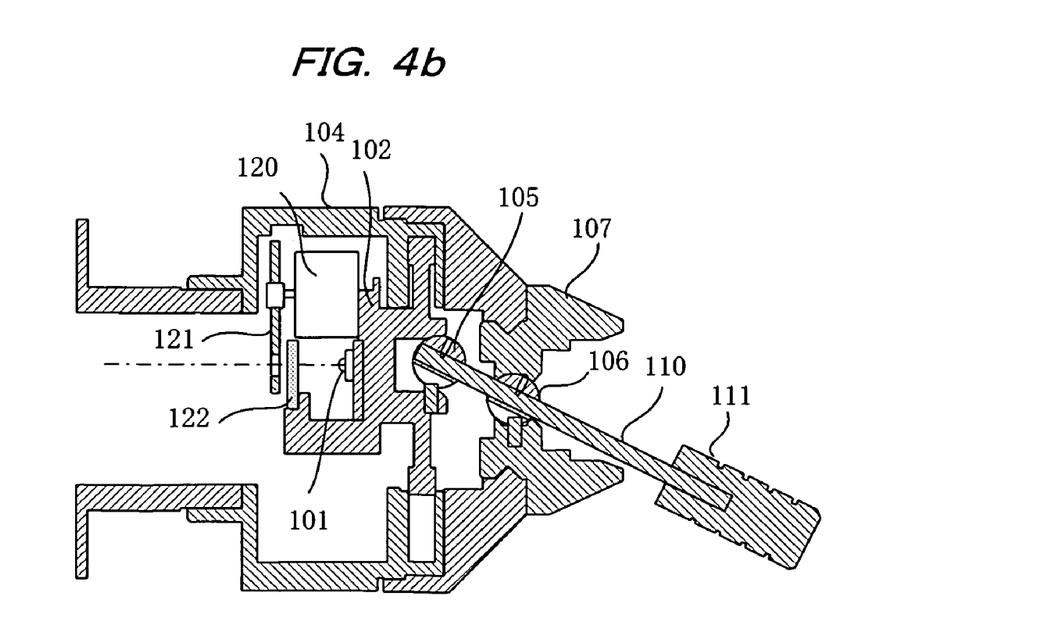
FIG. 4b is a longitudinal sectional view showing the stimulus light source unit when the operating lever is moved to the lower position.

FIGS. 4a and 4b show another embodiment of the stimulus light source unit.

Figure 5:
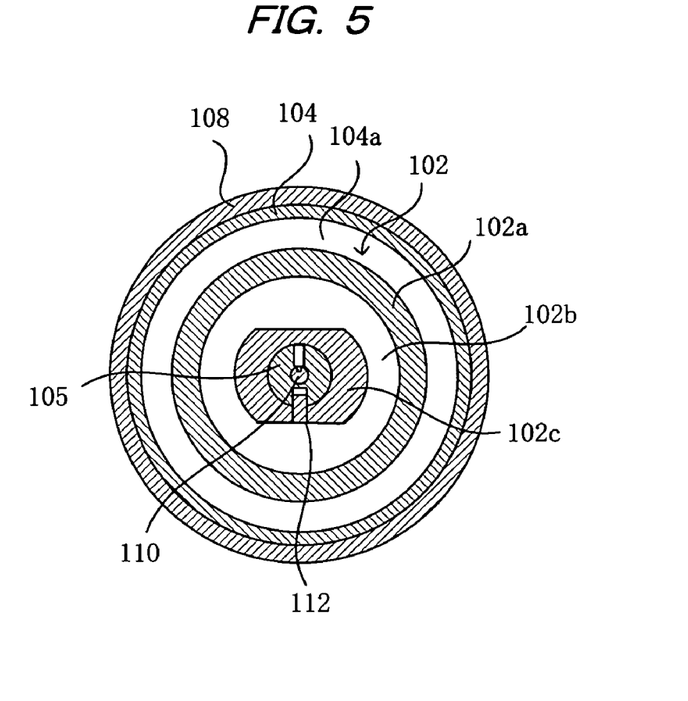

A stimulus light source unit 100 shown in FIG. 4 has a housing 104 fixed to the light stimulus unit 10. A light-emitting diode or other stimulus light source 101 for emitting the same visible light as the stimulus light source 51 is fixed to the side of a movable block 102 facing the unit 10 via an attachment panel 103 in the stimulus light source unit 100. The side of the movable block 102 opposite the unit 10 forms a disk having an external peripheral part 102a, an intermediate part 102b having a smaller width than the external peripheral part 102a, and a center part 102c that has a circular concave part 102d (see also FIG. 5). The external peripheral part 102a of the movable block 102 is engaged in a circumferential groove 104a formed within the housing 104 of the stimulus light source unit 100, and the concave part 102d of the center part 102c serves as a bearing support for supporting a spherical body 105 inserted therein so as to allow the spherical body 105 to rotate.

A bearing 107 for providing support so that a spherical body 106 can rotate is fixed to the housing 104 via a middle ring 108. The spherical bodies 105, 106 are pinned to the distal end part of a rod 110 of an operating lever 111, and the movable block 102 can move in the x-y plane perpendicular to the optical axis 130 of the stimulus light projection optical system through the use of the operating lever 111 that functions as an operating member via the spherical bodies 105, 106. Slits 105a, 106a are formed in the spherical bodies 105, 106, respectively. A stop pin 112 fixed to the center part 102c of the movable block 102, and a stop pin 113 fixed to the bearing 107 are engaged in the slits 105a, 106a, respectively. This allows the movable block 102 to be prevented from rotating about the optical axis 130.

Figure 7:
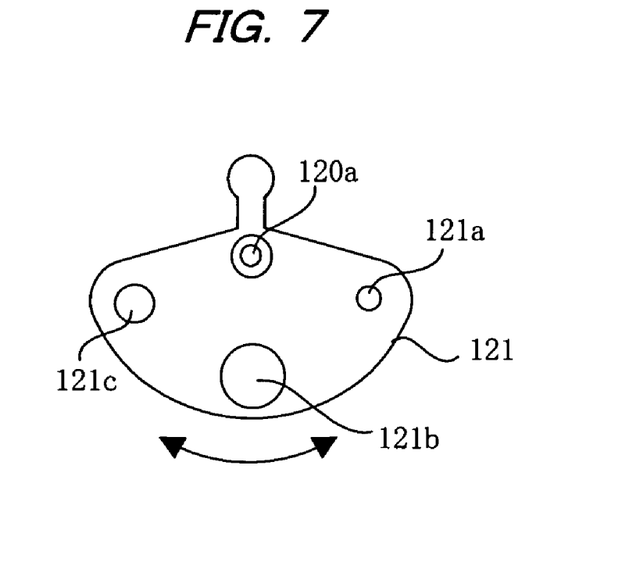
FIG. 7 is a front view showing an indicator panel.

An electric motor 120 composed of a stepping motor or the like is attached to the side of the movable block 102 opposite the operating lever 111 so that the motor shaft 120a is parallel to the optical axis 130. As shown in FIG. 7, an indicator panel 121 in which a plurality of openings 121a, 121b, 121c having different diameters is formed is attached to the motor shaft 120a in the x-y plane perpendicular to the optical axis 130. The indicator panel 121 is disposed in the same fundus conjugate position as the indicator disk 60 shown in FIG. 3, and rotates about the motor shaft 120a. The centers of the openings 121a, 121b, 121c of the indicator panel 121 are at equal distances from the motor shaft 120a. The spot size of the stimulus light can be varied by rotating the indicator panel 121 in the x-y plane perpendicular to the optical axis 130 and moving any of the openings to the position facing the stimulus light source 101. A diffusing plate 122 for diffusing the stimulus light is attached to a portion of the movable block 102 between the indicator panel 121 and the stimulus light source 101. Since the indicator panel 121 is attached to the movable block 102 via the electric motor 120, stimulus lights having different spot sizes can be placed in a prescribed position in the x-y plane perpendicular to the optical axis 130 by operating the operating lever 111.

In the stimulus light source unit 100 configured as described above, the movable block 102 and the stimulus light source 101 and indicator panel 121 fixed thereto move in the x and y directions on the x-y plane perpendicular to the optical axis 130 about the spherical body 106 when the examiner manually moves the operating lever 111 in the x-y direction.

Figure 6:
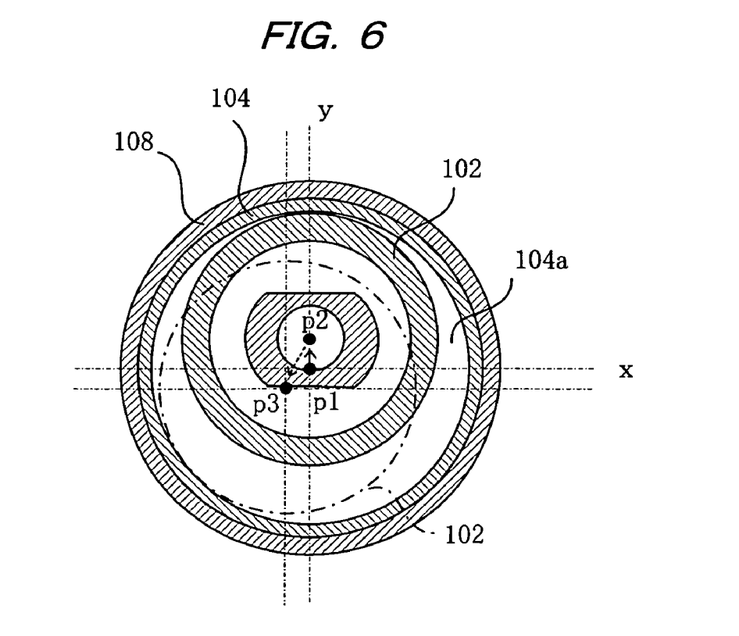
FIG. 6 is an illustrative view showing the movement of a movable block of the stimulus light source unit.

For example, when the operating lever 111 is moved from the state shown in FIG. 4a to the state shown in FIG. 4b to the lower limit in the y direction, the movable block 102 moves upward accordingly, and the position of the stimulus light source 101 moves as shown in FIG. 6 from the position P1 of the state shown in FIG. 4a to the position P2 of the state shown in FIG. 4b. By moving the operating lever 111 in the x-y direction, the movable block 102 can be arbitrarily moved within the range defined by the circumferential groove 104a of the housing 104. For example, the stimulus light source 101 can be placed in the position P3, as indicated by the dashed line in FIG. 6.

Any of the openings 121a, 121b, 121c of the indicator panel 121 can be moved to the position facing the stimulus light source 101 by rotating the indicator panel 121 about the motor shaft 120a. The size of the stimulus light can thus be changed by passing the stimulus light through the selected opening.

Such an arrangement allows the position of the stimulus light source 101 in the x-y plane perpendicular to the optical axis 130 as well as the spot size of the stimulus light to be varied in a wide range, and a satisfactory action potential and a reliable bioelectric signal can be generated from a wide range of the retina in the same manner as in the stimulus light source 50 shown in FIG. 2.

Figure 8:
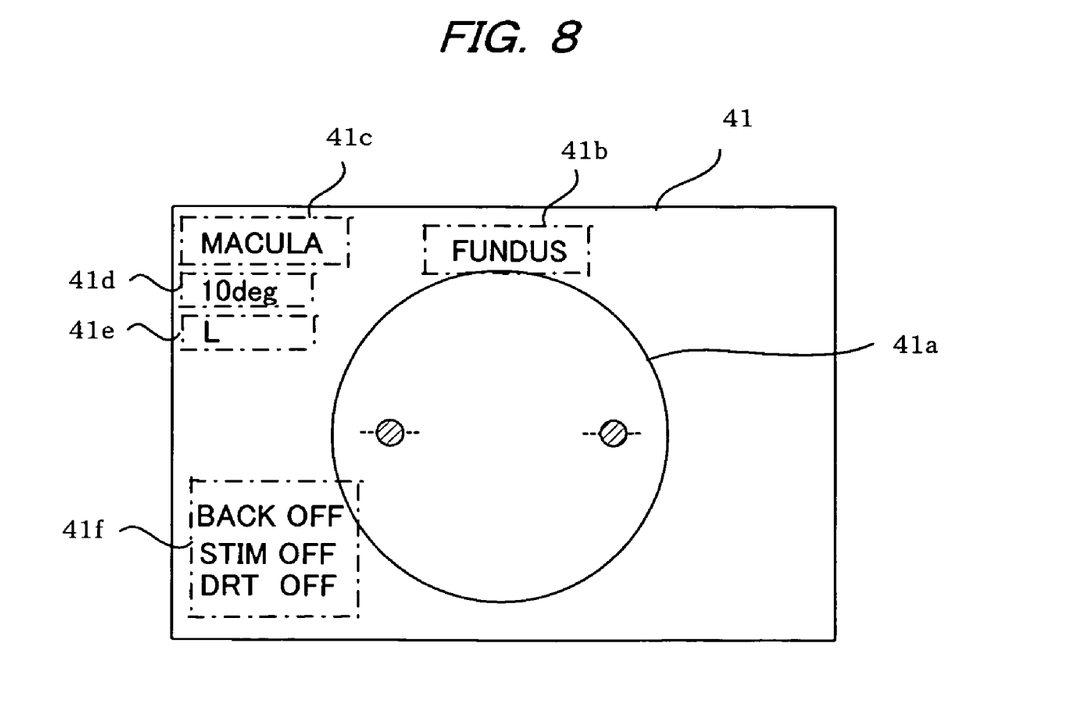
FIG. 8 is a screen view of a monitor for displaying the alignment state.

Since the size of the stimulus light can be known by the rotation position of the electric motor 120, the information of the rotation angle of the motor can be transmitted to the control unit 84, and the size of the stimulus light can be displayed on the monitor 41 as an angle of view on the retina, as indicated by the reference symbol 41d in FIG. 8. In FIG. 8, the reference symbol 41a indicates an alignment image, 41b indicates operation mode information, 41c indicates fixation lamp information, 41e indicates left/right eye information, and 41f indicates setting information for the background light, the stimulus light, and the stimulus light time.

In the stimulus light source unit 100 shown in FIG. 4, the indicator panel 121 is rotated merely by the electric motor 120, and a manual lever 62 for manual rotation is not provided, as in the stimulus light source unit 50 shown in FIG. 2. Therefore, it is possible to overcome the drawback in which the lever is erroneously operated during measurement, and the stimulus light size is changed.

Since the size information of the stimulus light is obtained from the motor rotation information, the size information can be displayed on the monitor, and the size of stimulus light being projected on the fundus during measurement can easily be known.

The movable block 102 must be prevented from rotating about the optical axis 130 because the electric motor 120 is mounted on the movable block 102 and the power cord to the electric motor should be prevented from being drawn into the stimulus light source unit 100. For this reason, the stop pins 112, 113 are provided as described above. In particular, the stop pin 113 is fixed to the bearing 107 that is attached so as to be unable to rotate with respect to the axis perpendicular to the x-y plane in the stimulus light source unit 100. Therefore, the movable block 102 and the stimulus light source 101 and indicator panel 121 attached to the movable block 102 can be prevented from rotating about the optical axis 130 or the axis parallel to the optical axis 130.

In the embodiment described above, the operating lever 111 is operated in order to change the projection position of the stimulus light onto the fundus. However, when the projection position of the stimulus light is determined and ERG measurement is performed, the examiner must maintain the operating lever in a constant position during measurement and make the projection position invariable. This creates the problem of increased burden on the examiner.

Figure 9:
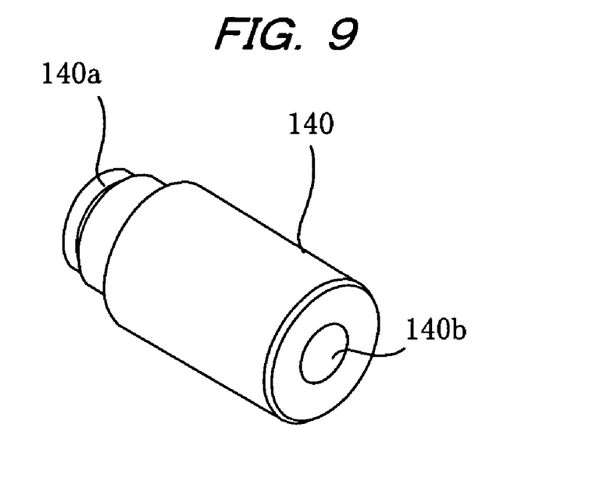
FIG. 9 is a perspective view showing a cap inserted into the stimulus light source unit to fix the operating lever.
Figure 10:
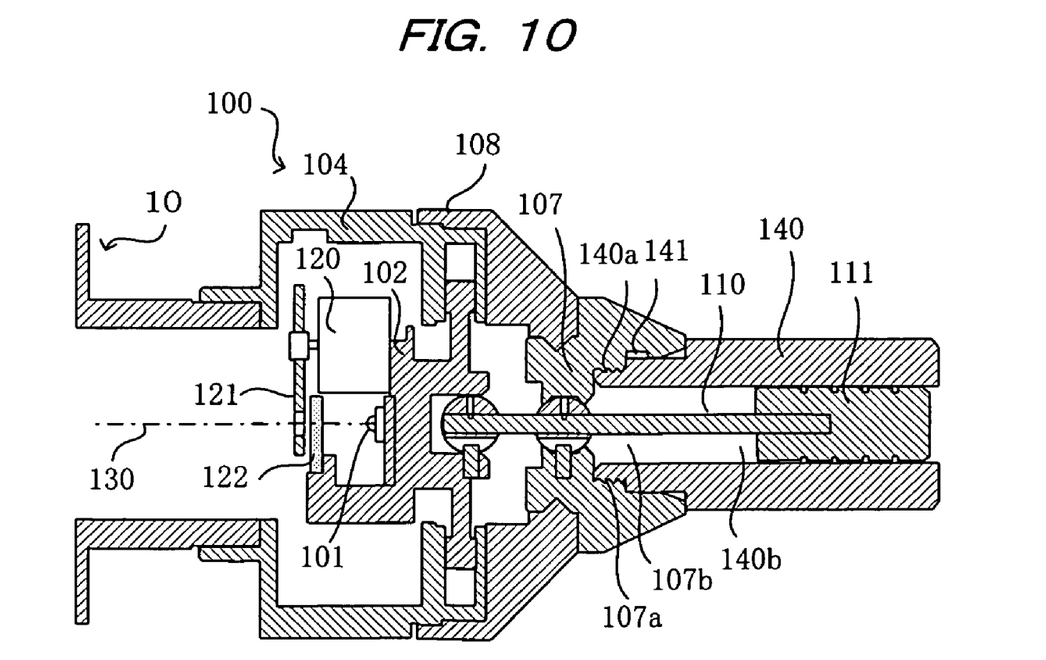
FIG. 10 is a longitudinal sectional view corresponding to FIG. 4a when the cap is inserted.

Therefore, as shown in FIGS. 9 and 10, the operating lever 111 is fixed to the main body of the stimulus light source unit 100 by a cap 140 that functions as a lock member or a fixing member. The distal end of the cap 140 forms a screw part 140a and a through-hole 140b is formed in the center thereof to lock the operating lever 111.

Since the inside diameter of the through-hole 140b of the cap 140 is slightly larger than the outside diameter of the operating lever 111, the operating lever 111 is inserted into the through-hole 140b of the cap 140, and the distal end of the cap 140 is fitted into a concave part 107b formed in the bearing part of the stimulus light source unit 100. This allows the movement of the operating lever 111 within the stimulus light source unit 100 to be locked to fix the projection position of the stimulus light. The cap 140 can be securely attached to the stimulus light source unit 100 by screwing together the screw part 140a of the cap 140 and the screw part 107a formed in the concave part of the bearing 107. Alternatively, the operating lever 111 can also be fixed by providing a concave part or a convex part to the cap 140, providing a convex part or concave part for fitting therewith to the operating lever 111, and fitting together the convex and concave parts of the cap 140 and operating lever 111.

Figure 11:
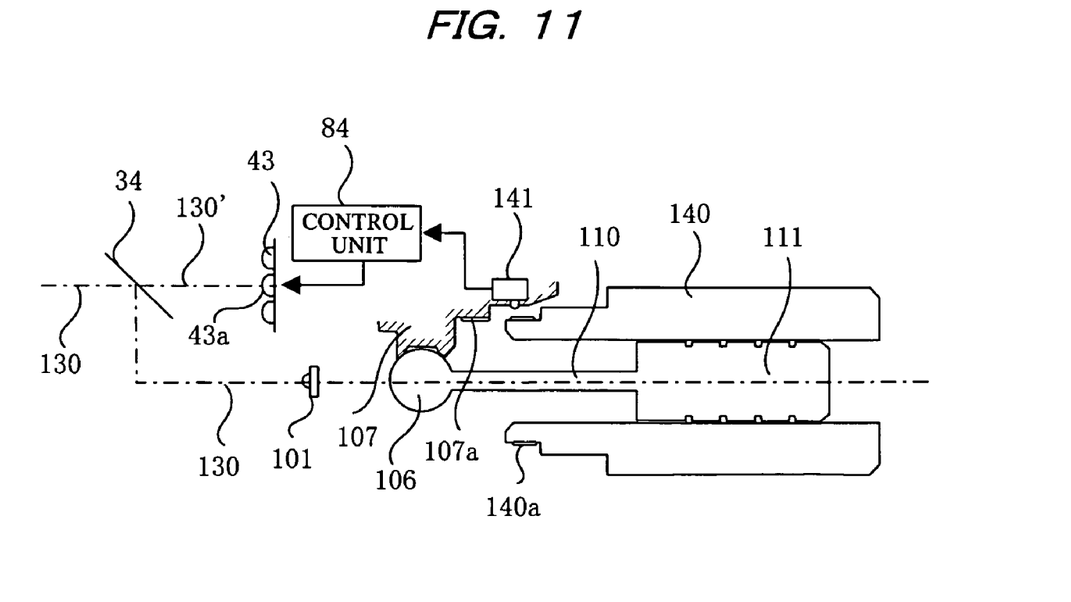
FIG. 11 is an illustrative view showing the structure for turning on the fixation lamp on the optical axis when the cap is inserted.

As shown in FIG. 4 or FIG. 10, the operating lever 111 is fixed when the rod 110 of the operating lever 111 is horizontal, and the stimulus light source 101 is positioned on the optical axis 130 of the stimulus light projection optical system. In this position, the stimulus light is referably designed so as to be projected onto the macula of the fundus to stimulate the macula. In order to achieve this, a microswitch 141 for detecting insertion of the cap 140 is attached inside the bearing 107. When the cap 140 is inserted in the stimulus light source unit 100, the microswitch 141 is activated to produce the ON signal that is inputted to the control unit 84, as shown in FIG. 11. The control unit 84 then turns on one fixation lamp 43a among the plurality of internal fixation lamps 43. Specifically, the internal fixation lamps 43 are disposed on a plane perpendicular to the optical axis 130' of an optical system that is branched from the stimulus light projection optical system by the mirror 34, as shown in FIGS. 1 and 11. When the cap 140 is inserted, the control unit 84 turns on a fixation lamp 43a positioned on the optical axis 130'. The projection optical system is configured so that the stimulus light is projected on the macula of the fundus when the examinee looks fixedly at the fixation lamp that is turned on.

Since the stimulus light source 101 and the selected internal fixation lamp 43a are each on the optical axis 130 when the macula is stimulated, the ERG examination can be performed without problems in the same position of the operating lever 111 regardless of whether the eye under examination changes to the left or right eye.

During macular stimulation, which is the most frequently performed operation in the ERG examination, the examiner can let go off the operating lever and perform the measurement because the operating lever can be fixed and immobilized. This allows the burden on the examiner to be reduced remarkably.

When the cap 140 is fitted to fix the operating lever 111, the operating lever 111 can be accommodated in the through-hole of the cap 140. This makes it possible to protect the operating lever during transporting of the apparatus.

What is claimed is:

1. An ocular light stimulus apparatus for providing localized light stimulus to a retina of an ocular fundus under examination to perform biological examination through use of a bioelectrical signal from the retina, comprising:
    a stimulus light source for emitting stimulus light to provide the localized light stimulus to the fundus under examination;
    a movement mechanism for moving the stimulus light source to change a projection position of the stimulus light on the fundus; and
    a stimulus light size changing mechanism for changing a size of the stimulus light from the stimulus light source.

2. An ocular light stimulus apparatus according to claim 1, wherein the stimulus light size changing mechanism moves in conjunction with movement of said stimulus light source.

3. An ocular light stimulus apparatus according to claim 1, wherein the stimulus light size changing mechanism includes an indicator panel having a plurality of openings with different diameters for allowing the stimulus light to pass through, the indicator panel being rotated about an axis parallel to an optical axis of a stimulus light projection optical system in a plane perpendicular to the optical axis in order to move one of the openings to a position facing the stimulus light source.

4. An ocular light stimulus apparatus according to claim 3, wherein the indicator panel moves together with the stimulus light source on a plane perpendicular to the optical axis of the stimulus light projection optical system.

5. An ocular light stimulus apparatus according to claim 3, wherein the indicator panel is rotated by an electric motor.

6. An ocular light stimulus apparatus according to claim 3, wherein the indicator panel and the stimulus light source are arranged so as to be unable to rotate about the optical axis or an axis parallel thereto.

7. An ocular light stimulus apparatus according to claim 1, wherein size information of the stimulus light that passes through a selected opening is displayed on a monitor for displaying alignment information.

8. An ocular light stimulus apparatus for providing localized light stimulus to a retina of an ocular fundus under examination to perform biological examination through use of a bioelectrical signal from the retina, comprising:

a stimulus light source for emitting stimulus light to provide the localized light stimulus to the fundus under examination;

a movement mechanism for moving the stimulus light source to change a projection position of the stimulus light on the fundus;

an operating member operated to act on the movement mechanism to change the projection position of the stimulus light; and a fixing member for fixing the operating member.

9. An ocular light stimulus apparatus according to claim 8, wherein the fixing member is configured as a cap having a through-hole in a center part thereof, the operating member being fixed by inserting the operating member in the through-hole of the cap and fitting the cap on a stimulus light source unit in which the stimulus light source is housed.

10. An ocular light stimulus apparatus according to claim 8, wherein the stimulus light source is positioned on the optical axis of the stimulus light projection optical system when the operating member is fixed.

11. An ocular light stimulus apparatus according to claim 10, wherein a plurality of internal fixation lamps is provided on a plane perpendicular to an optical axis of an optical system that is branched from the stimulus light projection optical system, and when the operating member is fixed, an internal fixation lamp positioned on the optical axis of the branched optical system is selected and turned on.

* * * * *